(12) United States Patent
Halpin

(10) Patent No.: US 9,408,722 B2
(45) Date of Patent: Aug. 9, 2016

(54) EXTERNAL BREAST PROSTHESIS

(71) Applicant: Sean P. Halpin, Rochester Hills, MI (US)

(72) Inventor: Sean P. Halpin, Rochester Hills, MI (US)

(*) Notice: Subject to any disclaimer, the term of this patent is extended or adjusted under 35 U.S.C. 154(b) by 0 days.

(21) Appl. No.: 14/053,180

(22) Filed: Oct. 14, 2013

(65) Prior Publication Data

US 2014/0046441 A1 Feb. 13, 2014

Related U.S. Application Data

(62) Division of application No. 12/915,365, filed on Oct. 29, 2010, now Pat. No. 8,557,168.

(60) Provisional application No. 61/255,910, filed on Oct. 29, 2009.

(51) Int. Cl.
| | |
|---|---|
| *A61F 2/52* | (2006.01) |
| *B29C 45/00* | (2006.01) |
| *A61F 2/50* | (2006.01) |
| *B29K 83/00* | (2006.01) |
| *B29L 31/00* | (2006.01) |

(52) U.S. Cl.
CPC ............... *A61F 2/52* (2013.01); *B29C 45/006* (2013.01); *A61F 2002/501* (2013.01); *A61F 2002/5053* (2013.01); *A61F 2002/526* (2013.01); *B29K 2083/00* (2013.01); *B29L 2031/7532* (2013.01)

(58) Field of Classification Search
CPC .................. A61F 2002/501; A61F 2002/5053; A61F 2002/526; A61F 2/52; B29K 2083/00; B29L 2031/7532

USPC ............................................................ 623/7
See application file for complete search history.

(56) References Cited

U.S. PATENT DOCUMENTS

| | | |
|---|---|---|
| 4,199,825 A | 4/1980 | Knoche |
| 4,600,551 A | 7/1986 | Erb |
| 4,676,795 A | 6/1987 | Grundei |
| 4,681,587 A | 7/1987 | Eberl et al. |
| 5,035,758 A | 7/1991 | Degler et al. |
| 5,376,323 A | 12/1994 | Eaton |
| 5,527,359 A | 6/1996 | Nakamura et al. |
| 5,603,791 A | 2/1997 | Weber-Unger et al. |
| 5,607,473 A | 3/1997 | Weber-Unger et al. |
| 5,700,288 A | 12/1997 | Eaton |
| 5,824,075 A | 10/1998 | Thielbar |
| 6,066,220 A | 5/2000 | Schneider-Nieskens |
| 6,086,801 A | 7/2000 | Eaton |
| 6,136,027 A | 10/2000 | Jackson |
| 6,162,250 A | 12/2000 | Malice, Jr. et al. |
| 6,451,139 B1 | 9/2002 | Weber-Unger et al. |
| 6,520,989 B1 | 2/2003 | Eaton |
| 6,564,086 B2 | 5/2003 | Marchitto et al. |
| 7,058,439 B2 | 6/2006 | Eaton et al. |
| 7,628,811 B1 * | 12/2009 | Gaskill ................. A61F 2/52 623/7 |
| 8,557,168 B2 | 10/2013 | Halpin |
| 2011/0125262 A1 | 5/2011 | Halpin |

* cited by examiner

*Primary Examiner* — Robert J Grun
(74) *Attorney, Agent, or Firm* — Ingrassia Fisher & Lorenz, P.C.

(57) ABSTRACT

An external breast prosthesis having a thin-walled outer shell and an air-filled interior cavity. The prosthesis is fabricated using a method and die set to form the two-part shell without internal supporting structure. The method provides a repeatable process which yields a prosthesis having durable airtight seal between the anterior and posterior shell and a Class-A exterior surface which accurately replicates the visual and tactile characteristics of a human breast.

14 Claims, 3 Drawing Sheets

EXTERNAL BREAST PROSTHESIS

CROSS-REFERENCE TO RELATED APPLICATIONS

This application is a divisional of U.S. patent application Ser. No. 12/915,365 filed on Oct. 29, 2010 which claims the benefit of U.S. Provisional Application No. 61/255,910, filed on Oct. 29, 2009. The entire disclosure of the above applications are incorporated herein by reference.

FIELD

The present disclosure relates to a breast prosthesis and method of fabricating same, and in particular to an external air-filled breast prosthesis having a human-like appearance.

BACKGROUND

This section provides background information related to the present disclosure which is not necessarily prior art.

The use of prosthesis is well known for the purpose of replicating or augmenting anatomical features of the human body, and in particular the human breast. To be acceptable, a breast prosthesis must accurately replicate the size and shape of the anatomy, as well as the function of such anatomy. In addition, the prosthesis must be ergonomically compatible and comfortable for the wearer.

The art is replete with various internal and external breast prostheses. In some instances, a relatively thin outer elastic shell is formed from an elastic silicone material. In these embodiments, the prosthesis is either made of solid silicon or the interior cavity of the prosthesis is filled with a material which provides internal support. Such filler materials may include various foams or other biocompatible fluids such as saline, silicone gel or natural triglyceride oils. These prostheses have a tendency to be heavy and/or inaccurate at replicating the form and function of the subject anatomy.

Accordingly, there is a need the art to provide an external breast prosthesis with a thin outer shell formed of an elastomeric material and an interior air-filled cavity, as well as a method and die set for fabricating such an external breast prosthesis.

SUMMARY

This section provides a general summary of the disclosure, and is not a comprehensive disclosure of its full scope or all of its features.

As further set forth in detail below, this disclosure provides an external breast prosthesis having a thin-walled outer shell and an air-filled internal cavity. The prosthesis is fabricated using a process and die set which provides a two part shell including an anterior cup-shaped portion and a posterior backer which when assembled defines an air-tight cavity. The nipple structure of the prosthesis is formed with a rayon flocking material having a fleshy color consisting of various tints of red, purple and gold. The outer shell is formed of an elastomeric material, preferably an elastic silicone material which has been vacuum treated to remove air that would otherwise cause bubbles, pits or voids in the thin-walled prosthesis. This disclosure further provides a method and die set for fabricating the thin-walled air-filled prosthesis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
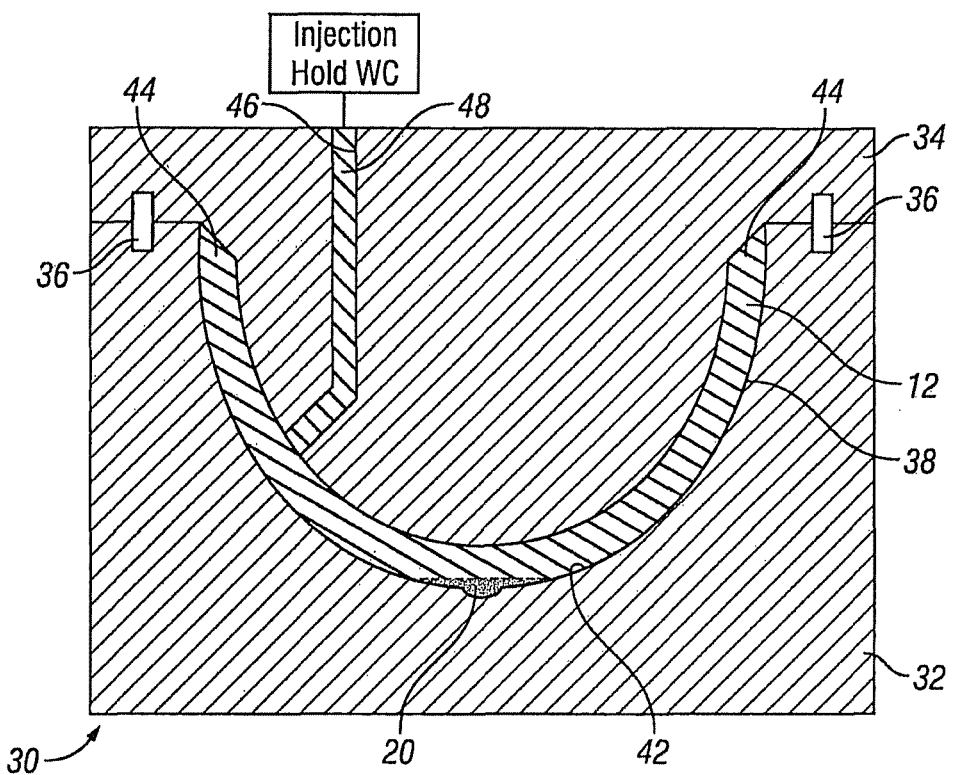
FIG. 1 illustrates a first mold assembly in which the anterior cup-shaped portion of the prosthesis is formed.

With reference now to the figures, an external breast prosthesis 10 having a thin-walled elastomeric shell 12, 16 with an air-filled interior cavity 18 is illustrated. In addition, the method and die set for fabricating this prosthesis is illustrated and described. With particular reference to FIGS. 1-3, the external breast prosthesis 10 includes a thin-walled anterior shell 12 having a perimeter edge portion 14 joined to a thin-walled posterior shell 16. In this configuration the anterior shell 12 and posterior shell 16 are arranged to define an air-filled interior cavity 18. The anterior shell 12 has a nipple/areola region 20 formed therein. As best seen in FIG. 3, the perimeter edge 14 of the anterior shell 12 is a chamfered perimeter edge 14 formed thereon which complements the edge defined by the posterior shell 16. In particular, the perimeter edge 14 bisects the interface between anterior shell 12 and posterior shell 16 to form a mitered joint. As noted above, the prosthesis is fabricated with an elastomeric material, preferably an elastic silicone material.

The breast prosthesis 10 is fabricated by injection molding the anterior shell 12 and then position forming the posterior shell 16 onto the anterior shell. The die sets 30, 50 used in this fabrication process sufficiently support the anterior shell 12 such that the prosthesis can be fabricated with an air-filled cavity and without internal support. In particular, a first mold assembly 30 as shown in FIG. 1 includes a lower die 32 and an upper cover 34. A series of pins 36 extend across the die separation surface and align the upper cover 34 with the lower die 32. The lower die 32 has a generally concave die cavity 38 formed therein. The bottom region 40 of the die cavity 38 is shaped to replicate the nipple/areola region of a human breast.

As presently preferred, the die cavity 38 is formed using a machining process which yields a Class-A exterior surface for the anterior shell 12 of the breast prosthesis 10. In particular, the interior die cavity 38 is machined to a precision surface based upon 3-dimensional modeling data similar to the techniques utilized in fabrication of automotive body panels. The upper die cover 34 has a generally convex surface 42 which complements the concave surface 38 formed on lower die 32. The convex surface 42 terminates at an angled annular surface 44 which defines the chamfered perimeter edge 14 on anterior shell 12. A gate 46 is formed through upper die cover 34 and extends into the cavity formed between concave surface 38 and convex surface 42. The gate 46 is coupled to an injection molding system 48 suitable for injecting an elastomeric material into the cavity.

A second die assembly 50 is provided which includes the lower die cavity 32 used in the first die assembly 30 and a die plate 52. The die plate 52 has a generally flat upper die surface 54 which may abut the perimeter edge 14 of the anterior shell 12 and extends inwardly towards the nipple/aerola region 20. As shown in FIG. 2B, the die cavity 32 is positionable into an abutting relationship with die plate 52 on a margin 56 which may be slightly relieved from the upper die surface 54. Gates 58 are formed in the margin 56 of the die plate 52 and extend from the horizontal surface to the boundary 60 of the die plate 52 for directing excess elastomeric material away from the prosthesis 10 during fabrication.

Figure 4:
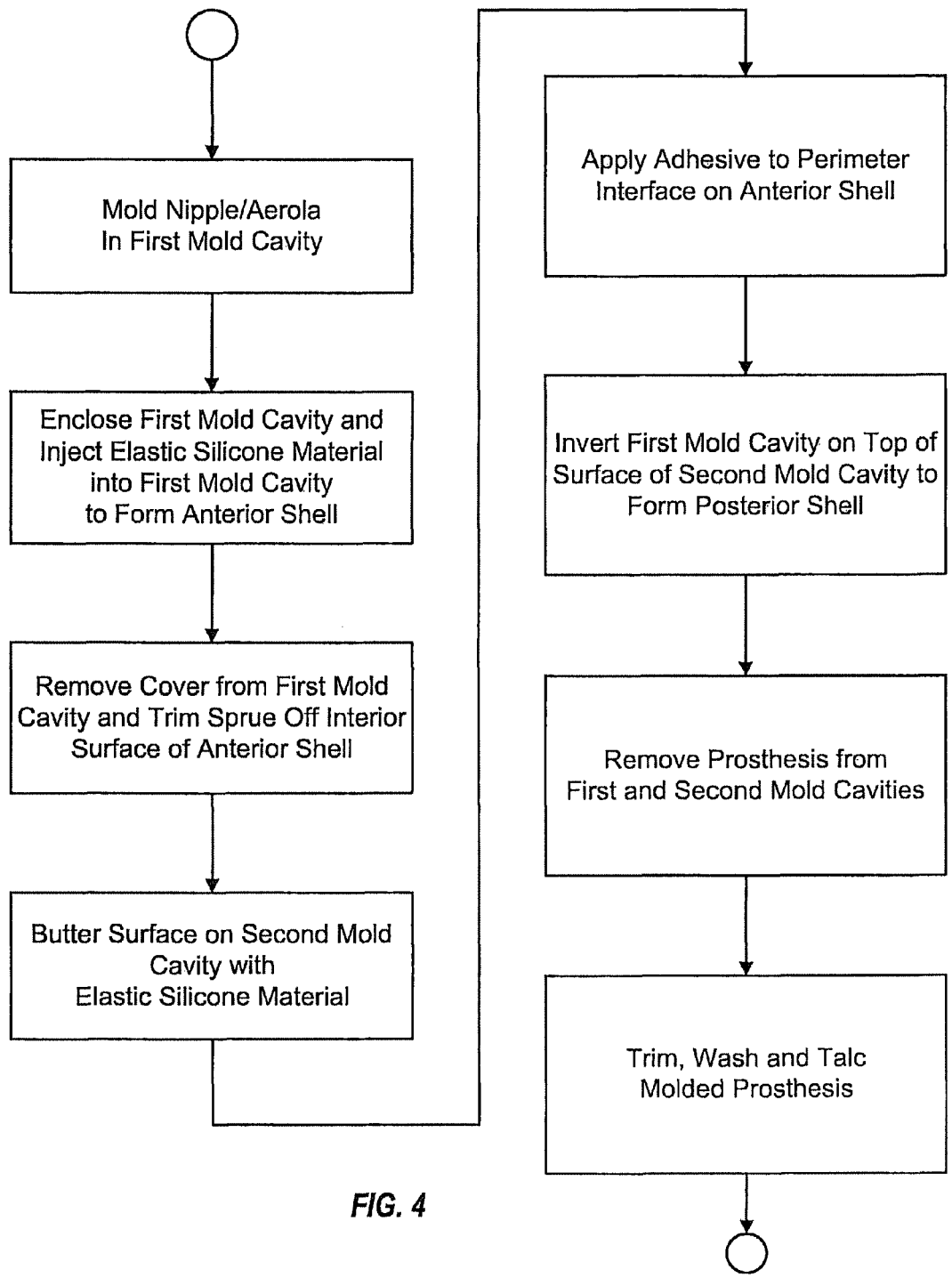
FIG. 4 is a flow chart setting forth the processing steps used in the fabrication of the breast prosthesis.

With reference now to FIG. 4, the fabrication process will be further explained. As presently preferred, a first mold cavity 32 is provided in an upright position with the concaved cavity facing upwardly. The nipple/areola region 20 of the breast prosthesis 10 is formed by depositing elastomeric material colored with pigments of red, purple and gold and mixed with rayon flocking fibers to simulate the color and texture of the nipple/areola region of a human breast. This material is permitted to partially cure.

While the nipple/aerola region cures, the first mold cavity 32 is enclosed with a die cover 34 yielding a thin-walled cavity to define what will become the anterior shell 12. Conventional injection molding process is used to inject elastomeric material into the first mold assembly 30 and form the anterior shell 12. The anterior shell 12 is allowed to substantially cure, typically for approximately four hours.

Once the anterior shell 12 is cured, the die cover 34 is removed from the die cavity 32 and the sprue 48 extending from the interior surface of anterior shell 12 is trimmed. A die plate 52 is provided with the upper surface 54 which is spread with a partially cured elastomeric material. In this regard, it is important that the elastomeric material be partially cured to a degree sufficient such that its viscosity will allow the elastomeric material to remain on the relatively flat horizontal surface 54 formed on die plate 52. Alternatively, the die plate 52 may be provided with a seal or similar feature around the boundary 60 for confining the elastomeric material on the upper surface 54.

A layer of adhesive 62 is applied to the perimeter edge 14 of the anterior shell 12. A suitable adhesive is selected to enhance adhesion and induce vulcanization or similar process in which the polymer molecules are linked to other polymer molecules by atomic bridges to form an air tight bond. While a vulcanization process in presently preferred, other acceptable processes such as similar thermostatic or thermoplastic processes may be utilized to achieve an air tight interface.

Figure 2A:
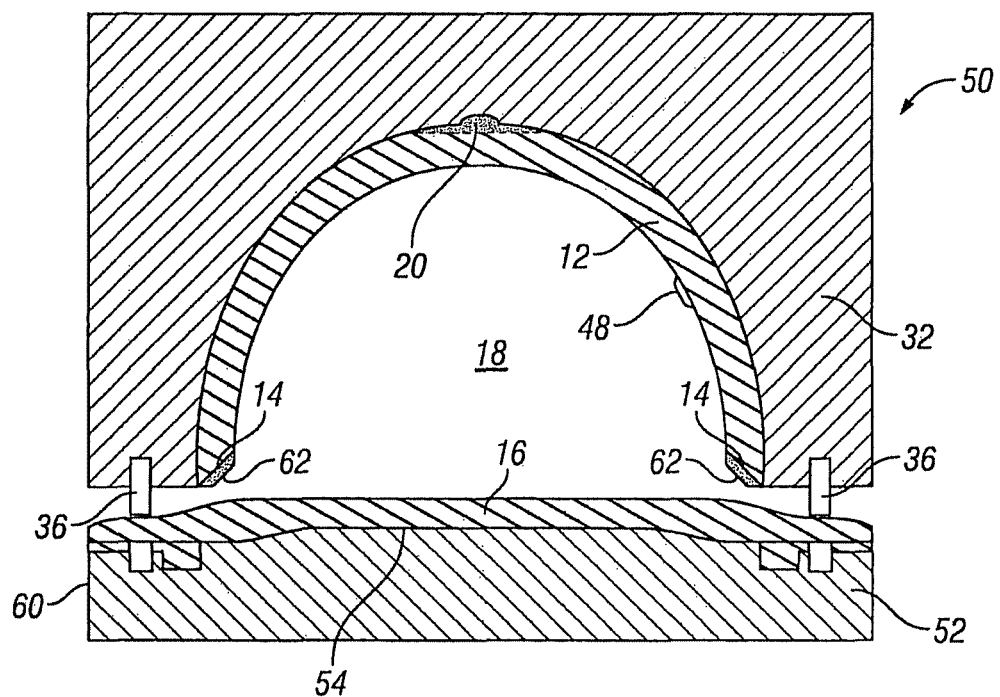
FIG. 2A illustrates a second molding assembly in a pre-assembled state with a thickened layer of elastic silicone material spread on the die plate.
Figure 2B:
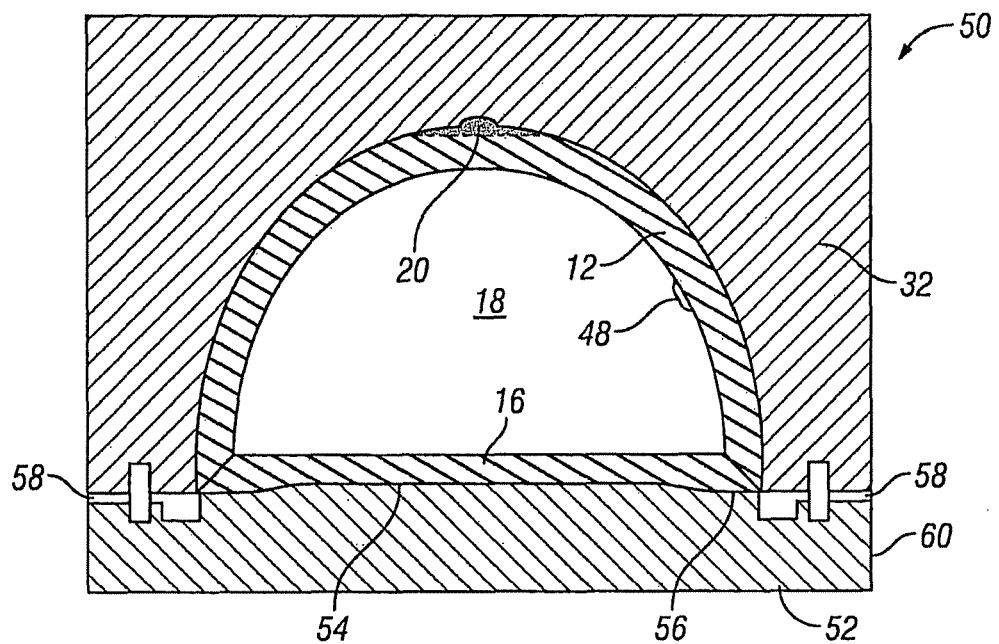
FIG. 2B illustrates the second molding assembly shown in FIG. 2A with the die cavity placed on top of the die plate.
Figure 3:
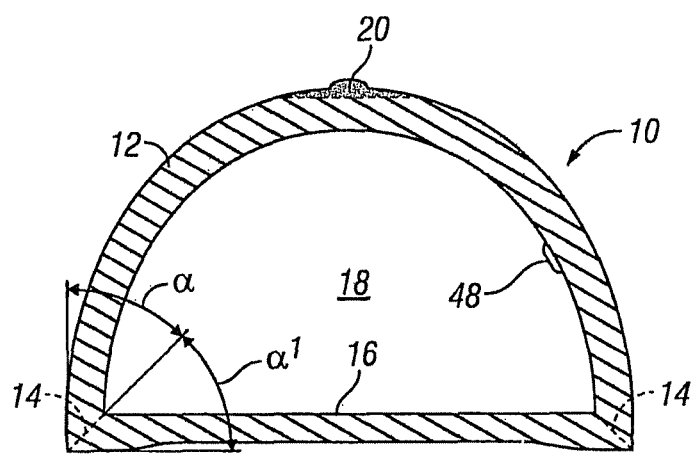
FIG. 3 is an illustration of the breast prosthesis in its finalized form.

Next, the die cavity 32 is rotated 180° from its position as shown in FIG. 1 into an inverted position as shown in FIGS. 2A and 2B. The die cavity 32 is then lowered on top of die plate 52 and aligned with pins 36 in a manner similar to that described with reference to FIG. 1. Sufficient adhesion exists between the anterior shell 12 and die cavity 32 to support the anterior shell 12 in the concave position above posterior portion 16. The interior cavity 18 defined by anterior shell 12 and posterior portion 16 captures ambient air to create air-filled interior cavity 18. The breast prosthesis 10 is allowed to fully cure, taking approximately three to six hours.

Once fully cured, the die plate 52 is removed form the die cavity 32. The breast prosthesis 10 is removed from die cavity 32. The molded breast 10 may include some flash material extending from the perimeter regions which may be trimmed using conventional processes. The breast prosthesis 10 is then washed and talced to provide an acceptable tactile characteristic simulating that of the human skin.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An external breast prosthesis comprising:
a posterior shell; and
an anterior shell defining a cup shaped body having a uniform wall thickness and a chamfered perimeter edge, the posterior shell covering the cup-shaped body to form an air-filled interior cavity;
wherein the chamfered perimeter edge forms a mitered joint between the anterior shell and the posterior shell.

2. The external breast prosthesis of claim 1 wherein the anterior shell and the posterior shell are formed with an elastomeric material.

3. The external breast prosthesis of claim 2 comprising further comprising an adhesive layer interposed between the chamfered perimeter edge and the posterior shell.

4. The external breast prosthesis of claim 1 comprising further comprising an areola region formed on a surface of the anterior shell opposite the posterior shell.

5. The external breast prosthesis of claim 4 wherein the areola region has a nipple formed therein.

6. The external breast prosthesis of claim 4 wherein the anterior shell, the areola region and the posterior shell are formed with an elastomeric material, the areola region further including a flocking fiber.

7. An external breast prosthesis comprising an elastomeric anterior shell defining a cup shaped body having a uniform wall thickness, an elastomeric posterior shell covering the cup-shaped body and forming an air-tight interior cavity, and an air-filled chamber consisting of an air volume sealed within the interior cavity, wherein the anterior shell, the posterior shell and the air-filled chamber define a valve-less prosthesis.

8. The external breast prosthesis of claim 7 wherein the anterior shell has a chamfered perimeter edge forming a mitered joint with the posterior shell.

9. The external breast prosthesis of claim 8 comprising further comprising an adhesive layer interposed between the chamfered perimeter edge and the posterior shell.

10. The external breast prosthesis of claim 7 comprising further comprising an areola region formed on a surface of the anterior shell opposite the posterior shell.

11. The external breast prosthesis of claim 10 wherein the areola region has a nipple formed therein.

12. The external breast prosthesis of claim 9 the areola region further including a flocking fiber.

13. The external breast prosthesis of claim 1 consisting of the anterior shell, the posterior shell, and the air-filled interior cavity.

14. The external breast prosthesis of claim 7 consisting of the anterior shell, the posterior shell, the interior cavity, and the air volume.

* * * * *